United States Patent [19]

Okamoto et al.

[11] Patent Number: 5,998,651
[45] Date of Patent: Dec. 7, 1999

[54] METHOD FOR FORMING ALKYL SILICATE

[75] Inventors: Hiroshi Okamoto, Owariasahi; Shin-ichi Inoue, Tokoname, both of Japan

[73] Assignee: Hiroshi Okamoto, Owariasahi, Japan

[21] Appl. No.: 09/266,786

[22] Filed: Mar. 12, 1999

[30] Foreign Application Priority Data

Mar. 13, 1998 [JP] Japan .................................. 10-063479

[51] Int. Cl.$^6$ ................. C07F 7/04; C07F 7/08; C07F 7/18
[52] U.S. Cl. .................. 556/470; 556/457; 556/458; 556/467
[58] Field of Search .................... 556/470, 467, 556/457, 458

[56] References Cited

U.S. PATENT DOCUMENTS 5,183,914  2/1993  Yeh et al. .............................. 556/467

*Primary Examiner*—Paul F. Shaver
*Attorney, Agent, or Firm*—Oblon, Spivak, McClelland, Maier & Neustadt, P.C.

[57] ABSTRACT

A method for forming alkyl silicate easily at low costs. The method comprises a reaction step of mixing and reacting an aqueous solution of sodium silicate, and a solution of alcohol or alkyl halide in a water-insoluble organic solvent, in the presence of a catalyst; and an isolating step of separating an organic layer from the reactive mixed solution and isolating a reaction product from the organic layer.

5 Claims, No Drawings

METHOD FOR FORMING ALKYL SILICATE

BACKGROUND OF THE INVENTION

1. Field of the Invention

This invention relates to a method for forming alkyl silicate in a single step.

2. Description of the Related Art

Metallic silicon has been used as high-functional materials for solar cells, semiconductors, etc. in view of its physical and chemical properties. The metallic silicon has to have a single crystal body in order to exhibit a higher function. For this reason, researches have been conducted on growth of single silicon crystal actively and extensively since 1950's, and some methods of producing crystals have been reported. Among them, the most general and most economic method is Czochralski process which was developed in 1918. However, Today's general method of synthesizing high-purity metallic silicon is to use easily available silicon dioxide as a raw material, mix silicon dioxide with a carbon reducing agent, heat the mixture above 2000° C., and continuously supply an electric power of 13 $MK^{wh}/t$.

However, silicon dioxide used as a raw material is synthesized from silicon tetrachloride or alkoxy silane. Alkoxy silane is synthesized from silicon tetrachloride, and silicon tetrachloride is synthesized from crude metallic silicon.

Due to these complicated synthesizing processes, high-purity metallic silicon is very expensive. So, the present inventors have studied about a method of obtaining inexpensive alkoxy silane by using cheap water glass as a raw material.

As for organic derivatives of water glass, few researches have been made since Eblemen produced an organic silicon compound in 1844. One of the few reports is that Kird made direct esterification of polymerized silicon in 1946, and another is that in 1947, Iler et al synthesized polyester silicate in a two-step reaction in which water glass was first treated by acid and then the resultant was reacted with alcohol.

SUMMARY OF THE INVENTION

The present invention has ben conceived in view of the above circumstances. It is an object of the present invention to form alkyl silicate in a single simple step.

Other objects and advantages of the present invention will become apparent from the detailed description to follow taken in conjunction with the appended claims.

The method for forming alkyl silicate according to the present invention comprises:

a reaction step of mixing and reacting an aqueous solution of sodium silicate, and a solution of alcohol or alkyl halide in a water-insoluble organic solvent, in the presence of an acid catalyst; and an isolating step of separating an organic layer from said reactive mixed solution and isolating a reaction product from said organic layer.

The aforementioned sodium silicate is preferably selected from the group consisting of sodium orthosilicate and water glass. The aforementioned alcohol or alkyl halide preferably includes an alkyl group having the carbon number of at least two. The aforementioned organic solvent is preferably selected from halogenated hydrocarbons such as chloroform, ethane dichloride, and trichloroethane.

The aforementioned catalyst is preferably selected from the group consisting of sulfuric acid, hydrochloric acid, copper chloride, tin chloride, hydrochloric acid and copper chloride, and hydrochloric acid and tin chloride.

DETAILED DESCRIPTION OF THE PRESENT INVENTION

In the method for forming alkyl silicate according to the present invention, an aqueous sodium silicate solution including a catalyst, and a solution of alcohol or alkyl halide in a water-insoluble organic solvent are mixed to carry out esterification in the boundary of both the solutions in the reaction step; and alkyl silicate generated dissolves in the organic solvent so as to be separated from unreacted sodium silicate, and a reaction product is easily isolated from the organic solvent in the isolating step.

In the method according to the present invention, esterification is carried out in a single step. Ester generated can be easily separated. Unreacted products are soluble in water and can be isolated without being mixed in an organic layer. Alkyl silicate can be produced easily at low costs.

The reaction mechanism is assumed as follows: sodium silicate existing in a water layer becomes a silanol group under catalysis by inorganic acid or the like, and the silanol group reacts with alkyl halide into esterification in the boundary between the water layer and the organic layer. The ester portion moves into the organic layer and ONa groups of remnant silicic acid are esterificated continuously in the boundary between the water layer and the organic layer. As the ester group exists in a larger volume, it becomes soluble in the organic layer and finally dissolves in the organic layer.

Examples of sodium silicate used in the present invention include sodium orthosilicate and water glass.

The alkyl group used for esterification is, for example, alkyl halide such as ethyl bromide, propyl bromide, butyl bromide, propyl chloride and butyl chloride.

The alcohol used here is water-insoluble alcohol such as ethyl alcohol, propyl alcohol, butyl alcohol, penthyl alcohol, and hexanol.

The organic solvent used here is preferably a water-insoluble alkyl halide solvent. Examples of this organic solvent include chloroform, ethane dichloride, trichlene, ethylene dichloride, perchloroethylene, and carbon tetrachloride. This organic solvent dissolves the aforementioned alkyl halide or alcohol and makes it react in the boundary with an aqueous sodium silicate solution and takes in and dissolves the generated alkyl silicate.

A catalyst used in the present invention may be inorganic acid, metal chloride, or both of them. Examples of the catalyst include sulfuric acid, hydrochloric acid, copper chloride, and tin chloride, When inorganic acid and metal chloride are used in combination, it is particularly preferably to employ the combination of hydrochloric acid and copper chloride, and the combination of hydrochloric acid and tin chloride.

Since it is assumed that sodium silicate becomes a free acid radical, silanol, and reacts with alcohol or alkyl halide, pH of the water layer is preferably acid.

Further, the reaction is made in a state that water drops are dispersed in an organic solvent. In order to increase the interface of the water and the organic solvent, it is desirable to stir the mixed solution vigorously. That is to say, it is desirable to use a mixer or other powerful stirring apparats.

In addition, it is preferable to carry out esterification around room temperature because a reverse reaction proceeds or the reaction is put in an equilibrium state at elevated temperatures.

The method according t the present invention has the following advantages.

Alkyl silicate can be synthesized at a relatively high yield rate by the reaction of sodium silicate and either of alkyl halide and alcohol in the boundary of water and an organic solvent. In addition, alkyl silicate can be easily obtained at room temperature by using an aqueous solution of inexpensive water glass. Moreover, generated alkyl silicate can be easily separated from unreacted silicic acid. Accordingly, the present inventive method can form alkyl silicate at low costs.

PREFERRED EMBODIMENTS OF THE PRESENT INVENTION

Hereinafter, the present invention will be described in detail by way of preferred embodiments.

In the reaction step, a predetermined amount of sodium silicate was dissolved in deionized water to prepare a dilute aqueous sodium silicate solution. On the other hand, a predetermined amount of alkyl halide or alcohol was dissolved in chloroform to prepare a reactive solution.

The aqueous solution and the organic solution were introduced into a reaction vessel at a ratio of 1:1, and inorganic acid and/or metal chloride as catalyst was added, and the resultant solution was vigorously stirred by a stirring apparatus at room temperature for a predetermined time.

In the isolation step, after the reaction was carried out for a predetermined time, the mixed solution was separated into the organic layer and the water layer, and a product was isolated from the organic layer. As for the reaction rates, the amount of alkyl halide remaining in the organic layer was determined by gas chromatography. The gas chromatograph used was "GC-8A" equipped with an integrator "C-R44" produced by Shimazu Inc. (Japan). the column used was "G-300", and nitrogen carrier gas was introduced at 1.0 kg/cm$^2$. Also, the amount of alkyl halide remaining in the organic layer was determined by nuclear magnetic resonance ($^1$H-NMR). The nuclear magnetic resonance spectra of the condensed organic layer was recorded with a spectrometer "Unity 300" produced by Varian Inc., and the chemical shifts were taken by using tetramethylsilane as internal standard. Also, the amount of alkyl halide was determined by Fourier transform infrared absorption spectrum (FT-IR).

The First Preferred Embodiment

A solution of an excessive amount of alkyl halide in chloroform was added to an aqueous sodium orthosilicate solution. Then copper chloride or tin chloride was added as catalyst and the mixed solution was vigorously stirred for 24 hours at room temperature so as to carry out esterification. The amount of each additive was as follows:

| | |
|---|---|
| Si(ONa)$_4$: | 0.5 × 10$^{-3}$ mol |
| CH$_3$CH$_2$Br: | 4.5 × 10$^{-3}$ mol |
| CH$_3$CH$_2$CH$_2$Br: | 6.2 × 10$^{-3}$ mol |
| CH$_3$CH$_2$CH$_2$Cl: | 2.3 × 10$^{-3}$ mol |
| CUCl$_2$: | 1.8 × 10$^{-3}$ mol |
| SnCl$_2$: | 1.8 × 10$^{-3}$ mol |

TABLE 1

| CATALYST | REACTION RATE (%) | | |
|---|---|---|---|
| | CH$_2$CH$_2$Br | CH$_3$CH$_2$CH$_2$Br | CH$_3$CH$_2$CH$_2$Cl |
| CuCl$_2$ | 67.6 (2.7) | 62.3 (2.5) | 35.7 (1.4) |
| SnCl$_2$ | 52.1 (0.6) | 21.9 (0.9) | 15.2 (0.6) |

* The numerals in brackets are the numbers of ONa groups replaced with alkyl groups. When 100% of them are replaced, the number is 4.0.

As apparent from Table 1, when copper chloride was used as catalyst, activity of esterification was observed with regard to all of ethyl bromide, n-propyl bromide, and n-propyl chloride. Above all, as for ethyl bromide and n-propyl bromide, three ONa groups of the silicon compound were replaced with ester groups. When tin chloride was used, esterification activity was slightly lower than that when copper chloride was employed, but the reaction proceeded.

The Second Preferred Embodiment

An aqueous solution of 0.5×10$^{-3}$ mol sodium orthosilicate, and a solution of one of 4.5×10$^{-3}$ mol ethyl bromide, 6.2×10$^{-3}$ mol n-propyl bromide, and 2.3×10$^{-3}$ mol n-propyl chloride in chloroform were introduced into an eggplant-shape flask at a ratio of 1:1, and 1.9×10$^{-2}$ mol sulfuric acid was added as catalyst. The mixed solution was vigorously stirred at room temperature to carry out a reaction. After the reaction, the solution was separated into the organic layer and the water layer. As for the reaction rate, the amount of alkyl halide remaining in the organic layer was determined by gas chromatography.

Table 2 shows the reaction time and the reaction rate. In the case of ethyl bromide two ONa groups were esterificated in about four hours. In the case of propyl bromide, approximately more than 90% of ONa groups were replaced with ester groups in three hours. In the case of propyl chloride, the reaction speed was slow.

TABLE 2

| REACTION TIME | REACTION RATE (%) | | |
|---|---|---|---|
| (hr.) | CH$_3$CH$_2$Br | CH$_3$CH$_2$CH$_2$Br | CH$_3$CH$_2$CH$_2$Cl |
| 1 | 19.8 (0.8) | 36.2 (1.4) | 0 |
| 2 | 29.0 (1.2) | 80.6 (3.2) | 19.9 (0.8) |
| 3 | — | 91.5 (3.7) | 6.1 (0.4) |
| 4 | 50.8 (2.0) | 71.6 (2.9) | 11.0 (0.4) |
| 5 | 45.1 (1.8) | 64.1 (2.6) | 8.2 (0.3) |
| 6 | 52.1 (2.1) | 68.0 (2.7) | 8.5 (0.3) |

*The numerals in brackets are the numbers of ONa groups replaced with alkyl groups. When 100% of them are replaced, the number is 4.0.

The Third Preferred Embodiment

The reaction was carried out in the same way as in the second preferred embodiment, except that added catalyst was 1.8×10$^{-3}$ mol copper chloride (CuCl$_2$). The reaction rate was 26% in one hour of reaction, and one ONa group was replaced with an ester group.

The Fourth Preferred Embodiment

The reaction was carried out in the same way as in the second preferred embodiment, except that the added catalyst was 3.4×10$^{-2}$ mol HCl, 3.4×10$^{-2}$ mol CuCl$_2$, or 1.8×10$^{-3}$ mol SnCl$_2$. The results are shown in Table 3. Approximately two ONa groups were replaced with ester groups in about two hours. This demonstrates that the mixture or inorganic acid and metal chloride is effective as catalyst for esterification.

TABLE 3

| REACTION TIME | REACTION RATE (%) | |
|---|---|---|
| (hr.) | HCl + CuCl$_2$ | HCl + SnCl$_2$ |
| 1 | 40.9 (1.6) | 43.6 (1.7) |
| 2 | 47.0 (1.9) | 45.9 (1.8) |
| 3 | 38.6 (1.5) | 31.1 (1.2) |
| 4 | 28.3 (1.1) | 27.4 (1.1) |
| 5 | 23.9 (1.0) | 22.2 (0.9) |
| 6 | 24.4 (1.0) | 24.8 (1.0) |

*The numerals in brackets are the numbers of ONa groups replaced with alkyl groups. When 100% of them are replaced, the number is 4.0.

The Fifth Preferred Embodiment

An aqueous solution of 0.08 mol water glass No. 3 and a solution of 0.8 mol n-propyl bromide in chloroform were mixed at a ratio of 1:10 and 1 ml (0.02 mol) of sulfuric acid was added as a catalyst. The mixed solution was vigorously stirred at room temperature to carry out a reaction for three hours. As a result, propyl silicate was obtained at the reaction rates of 73.1%.

The Sixth Preferred Embodiment

An aqueous solution of 0.08 ml water glass No. 3 and a solution of 0.8 mol n-propyl alcohol in chloroform were mixed at a ratio of 1:10 and 1.0 ml (0.02 mol) sulfuric acid was added as catalyst. The mixed solution was vigorously stirred at room temperature to carry out reaction for 24 hours. As a result, propyl silicate was obtained at the reaction rate of 52.8%.

The Seventh Preferred Embodiment

The alcohol concentration was varied in the process of the sixth preferred embodiment and the reaction was carried out for 24 hours at room temperature. The results are shown in Table 4. When n-propyl alcohol at the concentration of 0.1 mol was used, the yield rate was 55.3%. When isopropyl alcohol at the concentration of 0.2 mol was used, the yield rate was 38.5%. There is a tendency that the yield rate decreases as the concentration of alcohol increases.

TABLE 4

| CONCENTRATION | REACTION RATE (%) | |
|---|---|---|
| (mol) | $CH_3CH_2CH_2OH$ | $(CH_3)_2CHOH$ |
| 0.1 | 55.3 | 2.0 |
| 0.2 | 32.3 | 38.5 |
| 0.3 | 16.9 | 13.5 |
| 0.4 | 0.2 | 1.6 |

Comparative Example

An aqueous solution of $0.5 \times 10^{-3}$ mol sodium orthosilicate and either of a solution of $6.2 \times 10^{-3}$ mol propyl bromide in chloroform and a solution of $2.3 \times 10^{-3}$ mol propyl chloride in chloroform were mixed at a ratio of 1:1. The mixed solution was vigorously stirred at room temperature for 24 hours to carry out a reaction. The reaction rate was 0.34% in the case of the propyl bromide solution, and the reaction hardly proceeded in the case of the propyl chloride solution.

Obviously, many modifications and variations of the present invention are possible in the light of the above teachings. It is therefore to be understood that within the scope of the appended claims, the invention may be practiced otherwise than as specifically described.

What is claimed is:
1. A method for forming alkyl silicate, comprising:

a reaction step of mixing and reacting an aqueous solution of sodium silicate, and a solution of alcohol or alkyl halide in a water-insoluble organic solvent, in the presence of a catalyst; and an isolating step of separating an organic layer from said reactive mixed solution and isolating a product from said organic layer.

2. A method for forming alkyl silicate according to claim 1, wherein said sodium silicate is selected from the group consisting of sodium orthosilicate and water glass.

3. A method for forming alkyl silicate according to claim 1, wherein said alcohol or said alkyl halide is a chemical compound including an alkyl group having a carbon number of at least 2.

4. A method for forming alkyl silicate according to claim 1, wherein said organic solvent is a halogenated hydrocarbon selected from the group consisting of chloroform, ethane dichloride, and trichloroethane.

5. A method for forming alkyl silicate according to claim 1, wherein said catalyst is selected from the group consisting of sulfuric acid, hydrochloric acid, copper chloride, tin chloride, hydrochloric acid and copper chloride, and hydrochloric acid and tin chloride.

\* \* \* \* \*